United States Patent
Cole

(10) Patent No.: US 6,568,241 B2
(45) Date of Patent: May 27, 2003

(54) ISOLATED CALIBRATION ADAPTER FOR STERILE PRESSURE TRANSDUCER

(75) Inventor: James E. Cole, Ventura, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/103,283

(22) Filed: Mar. 21, 2002

(65) Prior Publication Data

US 2002/0095973 A1 Jul. 25, 2002

Related U.S. Application Data

(63) Continuation of application No. 09/228,254, filed on Jan. 11, 1999, now abandoned.

(51) Int. Cl.[7] .......................... G01L 27/00; A61B 5/021
(52) U.S. Cl. ........................ 73/1.57; 73/1.63; 73/1.69; 73/706; 600/485
(58) Field of Search ................................. 73/1.57, 1.62, 73/1.63, 1.64, 1.66, 1.67, 1.69, 706, 714, 756; 600/485, 490

(56) References Cited

U.S. PATENT DOCUMENTS

| | | | | |
|---|---|---|---|---|
| 3,777,546 A | | 12/1973 | Rollins | 73/1.57 |
| 3,863,504 A | * | 2/1975 | Borsangi | 73/706 |
| 4,342,218 A | | 8/1982 | Fox | 73/1.62 |
| 4,407,296 A | * | 10/1983 | Anderson | 73/706 X |
| 4,471,646 A | * | 9/1984 | Walker | 73/1.67 |
| 4,499,903 A | | 2/1985 | Furst et al. | 600/488 |
| 4,603,574 A | | 8/1986 | Norman | 73/1.57 |
| 4,610,256 A | * | 9/1986 | Wallace | 73/1.69 X |
| 4,658,829 A | * | 4/1987 | Wallace | 600/488 |
| 4,672,974 A | | 6/1987 | Lee | 73/740 X |
| 4,712,566 A | * | 12/1987 | Hök | 73/1.57 |
| 4,760,730 A | | 8/1988 | Frank et al. | 73/1.59 |
| 4,936,310 A | * | 6/1990 | Engström et al. | 73/1.61 X |
| 5,006,835 A | | 4/1991 | Griswold et al. | 340/626 |
| 5,063,936 A | * | 11/1991 | Sato et al. | 73/1.62 X |
| 5,133,358 A | | 7/1992 | Gustafson et al. | 600/488 |
| 5,203,340 A | * | 4/1993 | Gustafson et al. | 600/488 |
| 5,257,630 A | | 11/1993 | Broitman et al. | 73/726 X |
| 5,417,395 A | | 5/1995 | Fowler et al. | 248/221.3 |
| 5,691,478 A | | 11/1997 | Barry et al. | 73/721 |
| 5,752,918 A | | 5/1998 | Fowler et al. | 600/488 |
| 5,753,820 A | | 5/1998 | Reed et al. | 73/706 |

* cited by examiner

*Primary Examiner*—Thomas P. Noland
(74) *Attorney, Agent, or Firm*—James J. Murtha

(57) ABSTRACT

A pressure transducer calibration device is disclosed having a housing which defines a first and second chamber separated by a compliant barrier. Two ports are in fluid communication with the first chamber, and one port is in fluid communication with the second chamber. The first chamber is configured to be filled with fluid and connected, via a three-way stopcock, to a pressure monitoring line. The second chamber is configured to be connected in fluid communication with a pressure generation device. In operation, the transducer is isolated from the monitored pressure source. Fluid communication is established between the first chamber and the transducer. A known fluid pressure is applied to the second chamber such that the known fluid pressure is also applied to the first chamber through the compliant barrier. The pressure transducer is then calibrated based upon the known fluid pressure within the first chamber.

14 Claims, 3 Drawing Sheets

ISOLATED CALIBRATION ADAPTER FOR STERILE PRESSURE TRANSDUCER

This application is a continuation of application Ser. No. 09/228,254 filed Jan. 11, 1999, and now abandoned.

FIELD OF THE INVENTION

The present invention relates to an apparatus for use in calibrating pressure transducers, such as those used in hospitals to monitor a patient's blood pressure. More particularly, the present invention is an apparatus for use in a fluid pressure monitoring line that allows the system to be pressurized, for calibration, without contaminating the sterile fluid in the system or risking introduction of air into the patient's fluid line.

BACKGROUND

In the health care field it is often important to monitor body fluid pressures, such as blood pressure. Pressure transducers are used to continuously monitor such fluid pressures. The transducer includes a sensor which converts fluid pressure to an electrical signal corresponding to the pressure. The electrical signal is then converted to a visual display of the pressure. When measuring a patient's blood pressure, the transducer is usually connected to a fluid line coupled to the patient's circulatory system, such as via a catheter introduced into the body.

When monitoring fluid pressure in this and other fields, it is important to verify the accuracy of the pressure transducer, initially and periodically during operation. For example, the transducer is usually zeroed by opening the transducer to atmospheric pressure. The transducer is then calibrated by applying a known test pressure to the transducer and then comparing the transducer pressure reading with the known pressure. Testing the transducer accuracy can also detect malfunctions in the pressure monitoring system.

The fluid pressure line between the patient and the transducer should remain closed and sterile to prevent risk of patient contamination. However, when a test pressure is applied to the transducer fluid line from an external source, there is a risk of contaminating the fluid line. There is also the serious risk of introducing air into the fluid line, which could potentially result in a patient air embolus. Thus, there are some potentially serious problems which can arise when calibrating blood pressure transducers.

One known method of addressing these and other problems includes the use of a bacteria filter and a drip chamber to reduce the risk of patient contamination or air embolus. Although generally effective at avoiding the problems mentioned above, this method is complicated to set up and still requires careful monitoring.

Another method of calibrating a pressure transducer involves the use of negative pressure applied to the back side of the transducer to simulate positive pressure applied to the patient side of the transducer. Although this method avoids the risks associated with patient contamination or air embolism, it is a complicated procedure which is not as accurate as patient side positive pressure calibration.

Recently, modular pressure transducers have been developed having a reusable part and a disposable part. A flexible dome in the disposable part is configured to fit adjacent a reusable diaphragm. Fluid flows into the disposable part, while no fluid contacts the reusable part. Fluid pressure in the disposable part causes the dome to press against the diaphragm and the pressure sensor of the transducer. If the dome is not properly attached, erroneous pressure reading can result and the zero balance can shift. Therefore, it is important to know whether the dome is properly attached to the transducer before the system is connected to the patient.

It would be an advancement in the art to provide an apparatus and method for calibrating pressure transducers in which the fluid path of the pressure monitoring system is pressurized without a potential of injecting air into the patient or contaminating the sterile fluid in the system.

It would be a further advancement in the art to provide an apparatus and method for calibrating pressure transducers which verifies the operation and calibration of modular pressure transducers and domes.

Such an apparatus and method for calibrating pressure transducers is disclosed and claimed herein.

SUMMARY OF THE INVENTION

The present invention is directed to a pressure transducer calibration device for use in calibrating a pressure transducer. The calibration device includes a housing which defines a first and second chamber therein. The first and second chambers are separated by a compliant barrier, such as a balloon or other flexible material. A first and second fluid port are in fluid communication with the first chamber, and a third fluid port is in fluid communication with the second chamber.

In operation, the pressure transducer is connected to a fluid pressure monitoring line having a stopcock to control fluid flow in the pressure monitoring line. The stopcock preferably has three fluid ports. Two of the ports are connected to the pressure monitoring line, and the third port is connected to the transducer calibration device.

A removable cap disposed on the calibration device's first fluid port permits the first chamber to be filled with fluid, such as sterile saline, and thereafter sealed. The second fluid port is configured to be connected to the stopcock. Selective adjustment of the stopcock places the calibration device in fluid communication with the pressure transducer. The calibration device's third fluid port is preferably configured to be connected in fluid communication with a pressure generation device capable of producing a known fluid pressure.

In one embodiment, the compliant barrier is a balloon disposed within the housing. The balloon has an interior and exterior surface such that the interior surface is in fluid communication with the pressure generation device. The balloon transfers the known fluid pressure from the second chamber to the first chamber such that the pressures are equalized.

In another embodiment, the compliant barrier is an elastomeric tube providing fluid communication between the first and second fluid ports. The first chamber is defined as the interior of the elastomeric tube. The exterior surface of the elastomeric tube is in fluid communication with the second chamber, which is coupled to a pressure generation device. The known pressure in the second chamber is transferred into the first chamber via the elastomeric tube.

In a currently preferred embodiment, the first fluid port is a female luer fitting, the second fluid port is a male luer fitting, and the third fluid port is a female luer fitting. However, persons having ordinary skill in the art will appreciate that other fluid port configurations can be used to connect the calibration device to the monitoring line and to the pressure generation device.

The present invention also includes a method of calibrating a pressure transducer. In a currently preferred embodiment, the pressure transducer is connected to a patient for the purpose of monitoring blood pressure. In the method, the transducer is isolated from the patient, that is, the blood pressure monitoring line is closed to the patient.

A calibration device is coupled to the blood pressure monitoring line in fluid communication with the transducer. As described above, the calibration device includes a housing having two chambers therein. The chambers are separated by a compliant barrier. A known fluid pressure is applied to one chamber and transferred to the other chamber through the compliant barrier and ultimately to the pressure transducer. The pressure measured by the pressure transducer is then calibrated based upon the known fluid pressure within the chambers of the calibration device.

In a currently preferred embodiment of the method, the pressure transducer has a fluid pressure monitoring line and a stopcock in fluid communication with the pressure monitoring line. The fluid pressure monitoring line provides fluid communication between the transducer and a patient. The stopcock has three fluid ports. Two of the ports are connected to the pressure monitoring line and the other port is connected to the transducer calibration device. The stopcock is adjusted to provide fluid communication between the transducer calibration device and the pressure transducer. The first chamber of the calibration device is filled with fluid and capped. A known fluid pressure is applied to the second chamber, such that fluid pressure within the first and second chambers are equalized due to movement of the compliant barrier. The pressure transducer is then calibrated based upon the known fluid pressure within the first and second chambers.

The transducer calibration device within the scope of the present invention can also be used to zero balance the transducer without opening the system to the atmosphere and possible contamination. The calibration device allows the system to remain closed during a zero balancing procedure, eliminating the risk of contamination or air embolus.

In the method of zero balancing the transducer, the pressure within the second chamber is increased. This is conveniently accomplished by injecting a small amount of air, such as 0.05 cc, into the second chamber so that the pressure in the chamber is above about 100 mm Hg. This step is necessary to eliminate the build-up of pressure in the first chamber. The stopcock is adjusted to provide fluid communication between the transducer calibration device and the pressure transducer. Thus, the monitored pressure source is isolated from the transducer and the transducer calibration device. The pressure within the second chamber is released to atmospheric pressure. This causes the pressure within the first chamber to drop to atmospheric pressure through the compliant barrier. The pressure transducer is then zero balanced. The pressure transducer can also be calibrated at this time according to the method described above.

DESCRIPTION OF THE INVENTION

Figure 1:
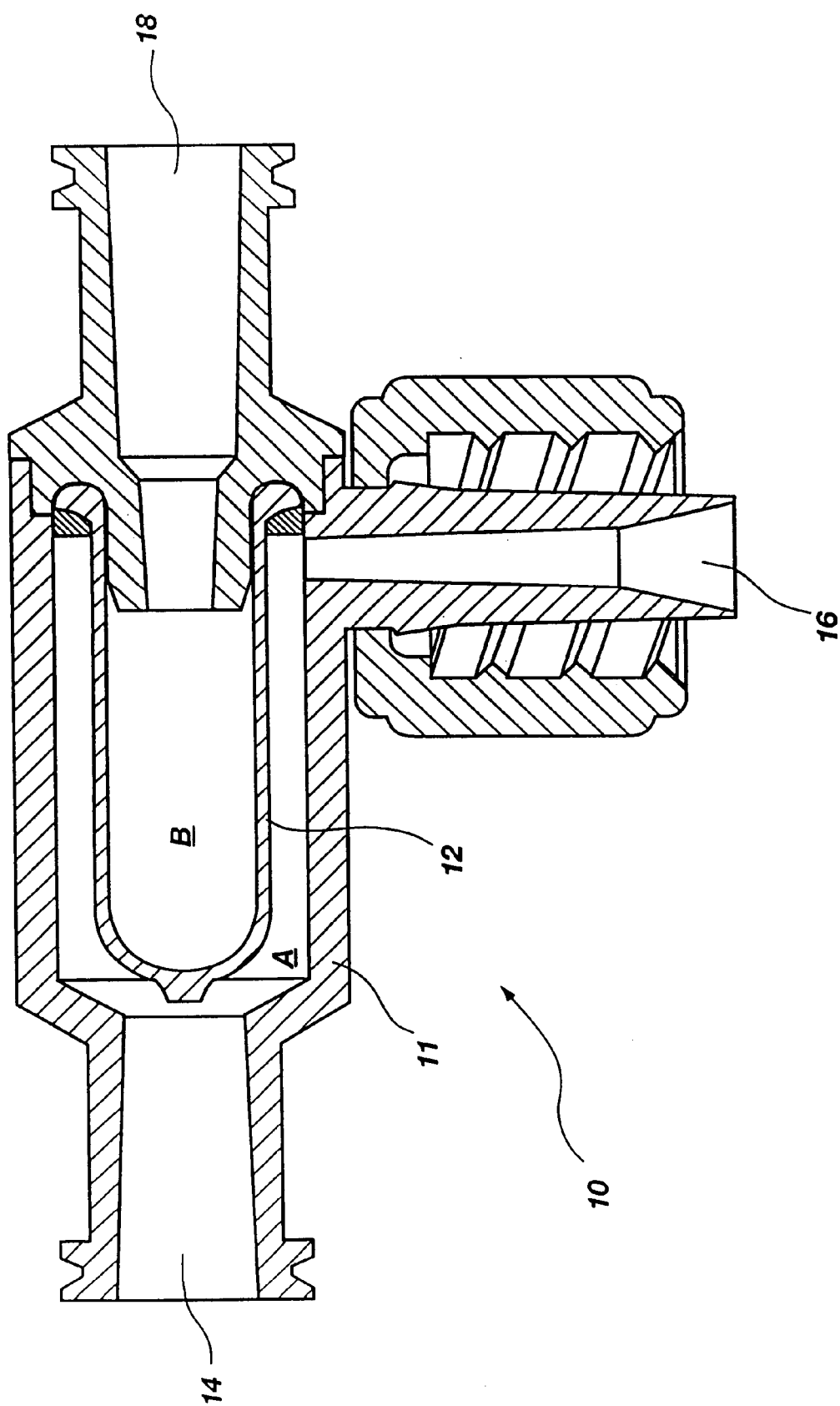
FIG. 1 is a cross-sectional view of one pressure transducer calibration device according to the present invention.

The present invention will now be described with reference to the figures. FIG. 1 shows one embodiment of a pressure transducer calibration device 10 within the scope of the present invention. The device 10 includes a housing 11 containing two chambers, labeled A and B, separated by a compliant barrier 12. To facilitate the manufacture and assembly of the device 10, the housing 11 may be constructed of a plurality of parts which are then joined together to form the device 10. In the device shown in FIG. 1, the compliant barrier is a balloon or bladder. Chamber (A) is in fluid communication with a first fluid port 14 and a second fluid port 16. Chamber (B) is in fluid communication with a third fluid port 18.

The first, second, and third fluid ports, 14, 16, 18, are preferably in the form of conventional luer fittings to facilitate fluid coupling to a pressure transducer system and pressure generation device, described below. As shown, the first and third fluid ports, 14 and 18, are preferably female luer fittings, while the second fluid port 16 is preferably a male luer fitting. Persons having ordinary skill in the art will appreciate that other port configurations are possible.

Figure 2:
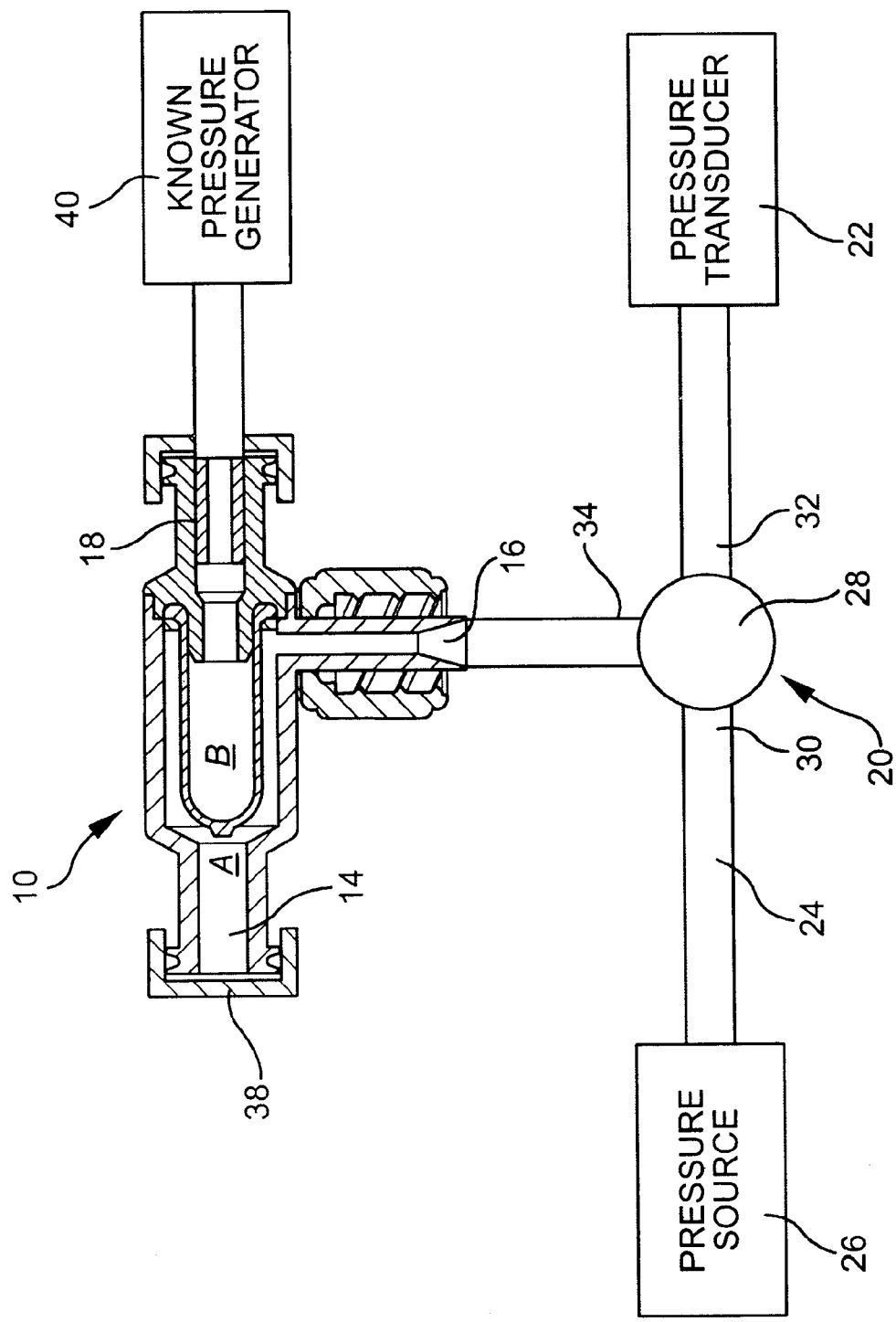
FIG. 2 is a schematic view of the pressure transducer calibration device shown in FIG. 1 coupled to a pressure transducer system.

Referring now to FIG. 2, a pressure transducer system 20, is illustrated. The pressure transducer system includes a pressure transducer 22. A pressure monitoring line 24 connects the transducer 22 with a monitored pressure source 26. The monitored pressure source 26 can be a patient in which blood pressure or other body fluid pressure is being monitored. The monitored pressure source 26 can be other pressure sources, including pressures which need to be monitored in industrial, manufacturing, transportation, health care, and energy production applications.

A three-way valve, or stopcock 28 is located in the pressure monitoring line 24 to provide controlled access to the monitoring line 24. The stopcock 28 is preferably a conventional stopcock having three fluid ports, a source port 30, a transducer port 32, and a calibration port 34. The source and transducer ports, 30 and 32, form part of the pressure monitoring line 24. The calibration port 34 is connected to the calibration device 10, preferably via the second fluid port 16. The stopcock 28 is configured to allow selective closure of fluid flow to the calibration device 10, while maintaining fluid flow through the pressure monitoring line 24. The stopcock 28 is also configured to allow closure of fluid flow to the monitored pressure source 26, while maintaining fluid flow between the calibration device 10 and the pressure transducer 22.

A removable cap 38 is disposed on the first fluid port 14. The removable cap 38 is configured to permit the first chamber A to be filled with fluid, such as sterile saline, and thereafter sealed.

The third fluid port 18 is preferably coupled to a pressure generation device 40. The pressure generating device 40 is capable of generating a known static pressure. When measuring blood pressure, for example, the pressure generating device preferably is capable of generating a static pressure from −300 to +300 mm Hg. The pressure generation device 40 can be a commercially available pressure generator, such as the "XCALIBER" pressure generator sold commercially by Becton Dickinson, or similar device such as the device disclosed in U.S. Pat. No. 4,658,829.

Figure 3:
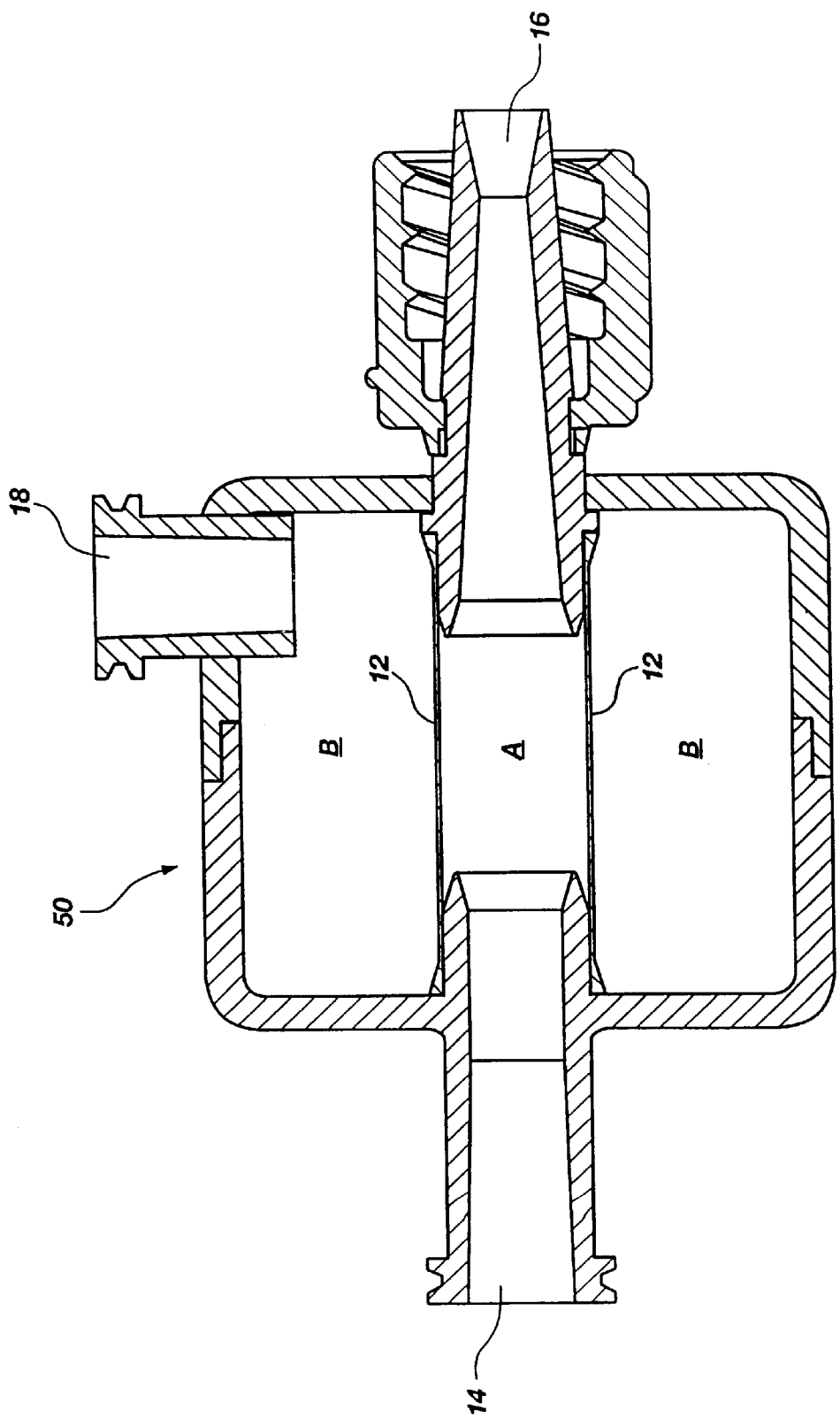
FIG. 3 is a cross-sectional view of another pressure transducer calibration device according to the present invention.

Another pressure transducer calibration device within the scope of the present invention is shown in FIG. 3. Calibration device 50 includes two chambers, labeled A and B, separated by a compliant barrier 12. Chamber (A) is in fluid communication with a first fluid port 14 and a second fluid port 16. Chamber (B) is in fluid communication with a third fluid port 18. In the device shown in FIG. 3, the compliant barrier 12 is an elastomeric tube providing fluid communication between the first and second fluid ports, 14 and 16.

The first, second, and third fluid ports of calibration device 50 are preferably. in the form of conventional luer fittings to facilitate fluid coupling to a pressure transducer system 20 and pressure generation device 40. As shown, the first and third fluid ports, 14 and 18, respectively, are preferably female luer fittings, while the second fluid port 16 is preferably a male luer fitting. Persons having ordinary skill in the art will appreciate that other port configurations are possible.

In use, the transducer calibration device, such as devices 10 or 50 described above, is attached to the calibration port 34 of the stopcock 28 in the pressure monitoring line 24. The calibration port can be used to zero the pressure transducer 22 according to conventional transducer calibration procedures or according to the zero balancing method described herein. The calibration device 10 can remain on the system 20 and be used to check the calibration as often as desired.

To calibrate the pressure transducer system 20 using the calibration device 10, one can perform the following steps:

1. Turn the lever on the stopcock "off" to the source port 30. This closes fluid flow between the monitored pressure source 26 and the transducer 22.

2. Remove the cap 38 on the first fluid port 14.

3. Fill chamber (A) and the first fluid port 14 with fluid, such as sterile saline.

4. Reapply the cap 38.

5. Zero balance pressure transducer 22 according to conventional procedures or according to the procedure described below.

6. Connect a pressure generation device 40 to the third fluid port 18.

7. Apply a known pressure to chamber (B) from the pressure generation device 40. This will pressurize the fluid in the system and allow calibration of the transducer 22.

8. Remove the pressure from chamber (B). Check that the pressure transducer 22 output reads zero.

9. Turn the lever on the stopcock "off" to the calibration port 34. This opens fluid communication between the monitored pressure source 26 and the transducer 22. The system 20 will now be measuring the monitored pressure source 26.

To zero balance the pressure transducer system 20 using the calibration device 10, one can perform the following steps:

1. Attach a 1 cc syringe to the third fluid port 18.

2. Inject about 0.05 cc of air into chamber (B) from the 1 cc syringe to increase the pressure in chamber (B) above about 100 mm Hg. This step is necessary each time, to eliminate the build-up of pressure within chamber (A).

3. While holding the air in chamber (B), turn the lever on the stopcock "off" to the source port 30. This closes fluid flow between the monitored pressure source 26 and the transducer 22, and it opens fluid flow between the calibration device 10 and the transducer 22.

4. Remove the syringe from the third fluid port 18. This will cause the pressure in both chambers (A) and (B) to drop to atmospheric pressure.

5. Zero balance the transducer. If desired, the transducer can be calibrated according to the method described above.

6. Turn the lever on the stopcock "off" to the calibration port 34. This opens fluid communication between the monitored pressure source 26 and the transducer 22. The system 20 will now be measuring the monitored pressure source 26.

An important feature of the method according to the present invention is the ability to calibrate a pressure transducer using positive pressure, without the risk of introducing contamination or air embolism into a patient. This is accomplished by the compliant barrier which is capable of transferring a known pressure, but which does not allow fluid, air, or contaminants to pass.

In the method of calibrating the pressure transducer, the transducer is isolated from the pressure source. This is most easily accomplished by closing the stopcock valve so that there is no fluid communication between the monitored pressure source and the pressure transducer. Turning the stopcock valve also establishes fluid communication between the first chamber of the calibration device and the pressure transducer. A known fluid pressure is applied to the second chamber. This pressure is conveyed to the first chamber through the compliant barrier. The pressure transducer is then calibrated based upon the known fluid pressure within the first chamber. Once properly calibrated, the transducer can then be reconnected to the monitored pressure source by turning the stopcock valve.

The transducer calibration devices 10 or 50 are preferably supplied in presterilized packages. They can also be supplied attached to pressure monitoring line 24 via stopcock 28 and presterilized.

It will be appreciated that the present invention provides an apparatus and method for calibrating pressure transducers in which the fluid path of the pressure monitoring system is pressurized without a potential of injecting air into the patient or contaminating the sterile fluid in the system. Such a device can be used to verify the operation and calibration of pressure transducers, including modular pressure transducers and domes.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

What is claimed is:

1. A pressure transducer calibration device adapted for connection between a pressure transducer and a pressure generation device including:

a housing defining a first chamber and a second chamber therein, wherein the first chamber and the second chamber are separated by a compliant barrier within the housing for transmitting positive fluid pressure between the first chamber and the second chamber;

a first fluid port in fluid communication with the first chamber and selectively connected to a pressure transducer disposed external to the housing;

a second fluid port in fluid communication with the first chamber and sealed to prevent fluid flow therethrough;

a third fluid port in fluid communication with the second chamber and operably connected to a pressure generation device.

2. The pressure transducer calibration device of claim 1 wherein the compliant barrier is a balloon.

3. The pressure transducer calibration device of claim 1 wherein the compliant barrier is an elastomeric tube.

4. The pressure transducer calibration device of claim 1 further comprising a means for selectively connecting the pressure transducer to a monitored pressure source.

5. A fluid pressure monitoring line configured to have one end connected to a patient and another end connected to, but isolated from a pressure transducer including:

a stopcock in fluid communication with the pressure monitoring line, the stopcock having three fluid ports, wherein two of the fluid ports are connected to the pressure monitoring line and one of the fluid ports is connected to a calibration device;

wherein the calibration device includes:

a housing defining a first chamber and a second chamber separated by a compliant barrier for transmitting positive fluid pressure between the first chamber and the second chamber;

a first fluid port and a second fluid port in fluid communication with the first chamber; wherein the first fluid port is selectively connected to a pressure transducer;

a removable cap disposed on the second fluid port, configured to permit the first chamber to be filled with fluid and thereafter sealed; and a third fluid port in fluid communication with the second chamber configured to be connected in fluid communication with a pressure generation device.

6. A fluid pressure monitoring line according to claim 5, wherein the compliant barrier is a balloon.

7. A fluid pressure monitoring line according to claim 5, wherein the compliant barrier is a balloon disposed within the housing, wherein the balloon has an interior and exterior surface such that the interior surface is in fluid communication with the third fluid port.

8. A fluid pressure monitoring line according to claim 5, wherein the compliant barrier is an elastomeric tube providing fluid communication between the first and second fluid ports.

9. A fluid pressure monitoring line according top claim 5, wherein the first fluid port is a female luer fitting.

10. A fluid pressure monitoring line according to claim 5, wherein the second fluid port is a male luer fitting.

11. A fluid pressure monitoring line according to claim 5, wherein the third fluid port is a female luer fitting.

12. A pressure transducer calibration device according to claim 5, wherein the first fluid port is a female luer fitting, the second fluid port is a male luer fitting, and the third fluid port is a female luer fitting.

13. A pressure transducer calibration device according to claim 5, wherein the compliant barrier is a balloon disposed within the housing, wherein the balloon has an interior and exterior surface such that the interior surface is in fluid communication with the third fluid port, wherein the first fluid port is a female luer fitting, the second fluid port is a male luer fitting, and the third fluid port is a female luer fitting.

14. A pressure transducer calibration device according to claim 5, wherein the compliant barrier is an elastomeric tube in fluid communication between the first and second fluid ports, wherein the first fluid port is a female luer fitting, the second fluid port is a male luer fitting, and the third fluid port is a female luer fitting.

* * * * *